(12) United States Patent
Larsen et al.

(10) Patent No.: US 6,693,203 B2
(45) Date of Patent: Feb. 17, 2004

(54) PROCESS FOR THE PREPARATION OF PGD2 ANTAGONIST

(75) Inventors: Robert Larsen, Rahway, NJ (US); Dongwei Cai, Rahway, NJ (US); Michel Journet, Rahway, NJ (US); Kevin Campos, Rahway, NJ (US)

(73) Assignee: Shionogi & Co., LTD, Osaka (JP)

( * ) Notice: Subject to any disclaimer, the term of this patent is extended or adjusted under 35 U.S.C. 154(b) by 0 days.

(21) Appl. No.: 10/398,741

(22) PCT Filed: Oct. 16, 2001

(86) PCT No.: PCT/US01/42763
§ 371 (c)(1), (2), (4) Date: Jun. 6, 2003

(87) PCT Pub. No.: WO02/32892
PCT Pub. Date: Apr. 25, 2002

(65) Prior Publication Data
US 2003/0199702 A1 Oct. 23, 2003

Related U.S. Application Data

(60) Provisional application No. 60/241,027, filed on Oct. 17, 2000.

(51) Int. Cl.$^7$ ............................................. C07D 333/56
(52) U.S. Cl. ......................................................... 549/58
(58) Field of Search ........................................... 549/58

(56) References Cited

U.S. PATENT DOCUMENTS 6,083,974 A 7/2000 Honma et al.
6,217,642 B1 4/2001 Kunisch et al.

*Primary Examiner*—Amelia Owens
(74) *Attorney, Agent, or Firm*—Foley and Lardner

(57) ABSTRACT

The present invention provides an efficient process for the preparation of benzothiophenecarboxamide PGD2 antagonist, S-5751.

4 Claims, No Drawings

PROCESS FOR THE PREPARATION OF PGD2 ANTAGONIST

BACKGROUND OF THE INVENTION

The benzothiophenecarboxamide derivative S-5751 (8) is a PGD$_2$ receptor antaongist potentially useful for the treatment of allergic rhinitis (including relieve of nasal congestion), asthma, allergic conjunctivitis, urticaria, ischemic reperfusion injury, inflammation, and atopic dermatitis. The compound is disclosed in PCT Published Application WO98/25919, which also describes its synthesis as shown below:

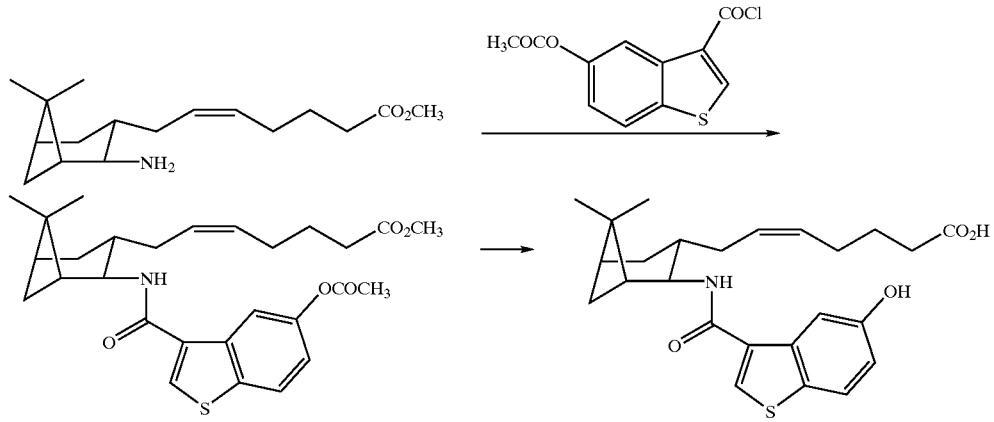

The preparation of the starting material aminoalkene ester is referenced to U.S. Pat. No. 4,904,819, which describes the synthesis as shown below:

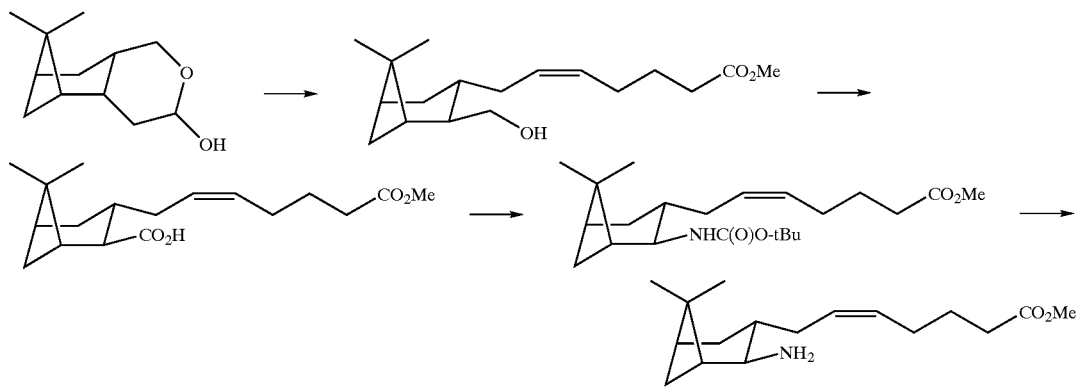

Another process for the preparation of S-5751 is disclosed in WO99/50261 as shown below:

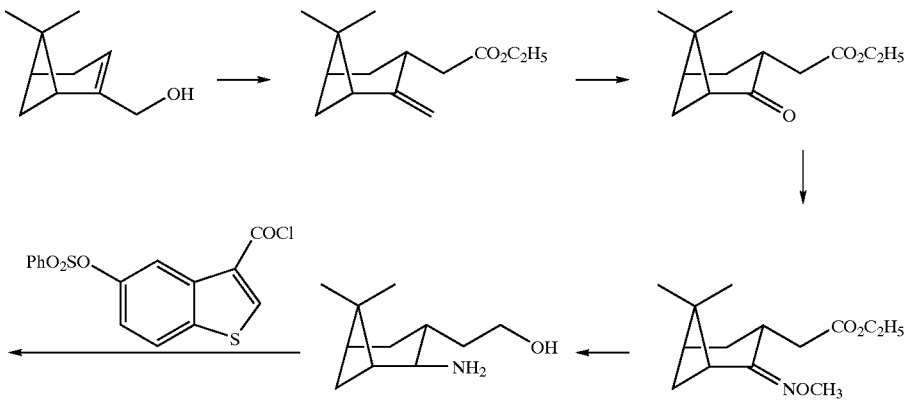

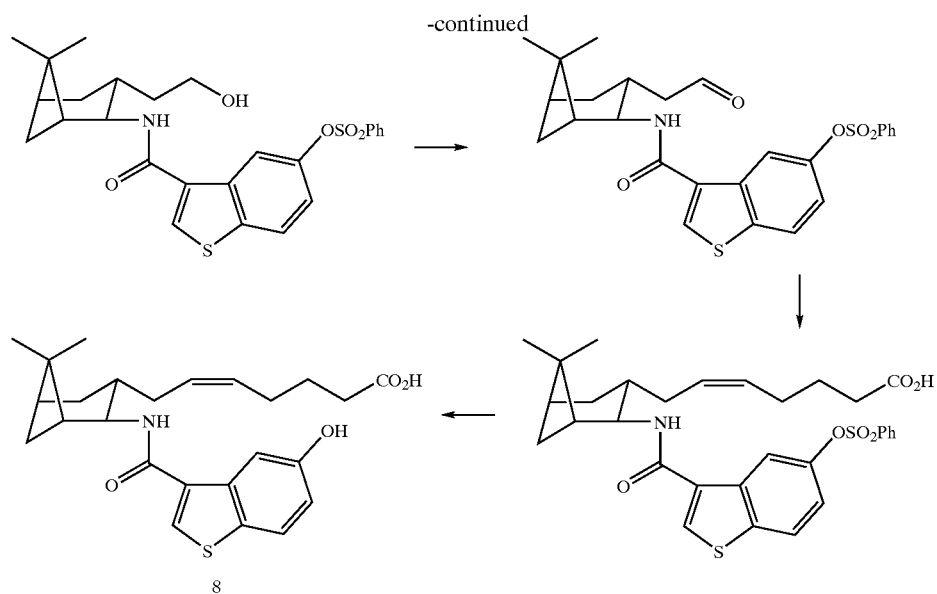

The reported synthesis of S-5751 are not modular or convergent, include superfluous oxidation/reduction steps at the ester group, or require specilized equipment, and therefore are not suitable for scale-up production and are uneconomical to run.

SUMMARY OF THE INVENTION

The present application relates to an efficient process for the preparation of the PGD2 antagonist S-5751

DETAILED DESCRIPTION OF THE INVENTION

The process of the present invention is schematically shown below:

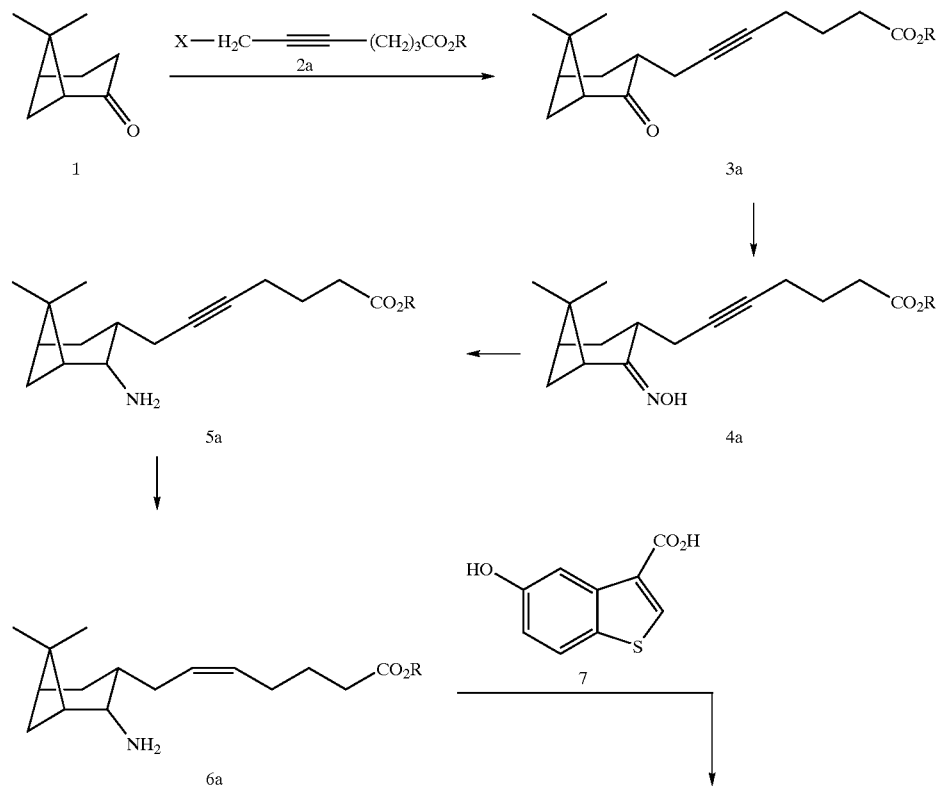

-continued

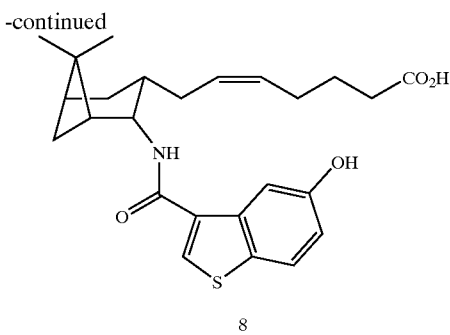

wherein X is a leaving group and R is a $C_{1-5}$ alkyl or a benzyl group.

The present process starts with the commercially available (1R)-(+)-nopinone 1. In the first step, the 5-heptynoate side chain 2a is attached to the (1R)-(+)-nopinone via alkylation of the enolate generated by treating the nopinone with a strong base to form the keto alkyne ester 3a. The preferred base for the reaction is lithium diisopropylamide. The leaving group of the heptynoate side chain 2a may be a halide such as chloride, bromide or iodide, or a sulfonate such as tosylate, mesylate or triflate, and the ester group may be a straight or branched alkyl group or a benzyl group; preferably the heptynoate side chain is ethyl 7-iodo-5-heptynoate. The reaction is conducted in an aprotic organic solvent such as tetrahydrofuran or other ethers such as methyl t-butyl ether or ethyl ether, and preferably in the presence of an amine base such as triethylamine. The reaction temperature is from about −50 to about −10° C., preferabably at about −50 to about −45° C. Reaction generally complete within about one to two hours. Acid, such as trifluoroacetic acid is added to the reaction mixture to quench base that can cause epimerization upon warming the reaction mixture to room temperature. The reaction product contains predominantly the desired diastereomer with a diastereomeric excess (d.e.) of 98% or greater.

In the second step, the keto alkyne ester 3a is converted to the corresponding oxime 4a using conventional methodologies. The keto alkyne ester 3a is treated with hydroxylamine hydrochloride in the presence of sodium acetate which acts as a base and buffer to neutralize HCl salt of hydroxylamine, and the reaction is carried out in a protic solvent such as an alcohol or water or a mixture thereof, and at elevated temperature preferably at about 50° C., and is complete within about 5 hours In the third step, the oxime 4a is reduced to the corresponding primary amine alkyne ester 5a. The oxime is first treated with titanium (III) chloride at temperature below about 10° C. to give the corresponding imine intermediate. The conversion to the imine is complete in about one hour, after which time a reducing agent such as borane is added and the reaction temperature is maintained at below about 10° C. until the imine to amine conversion is complete.

In the fourth step, the amine alkyne ester 5a is reduced to the corresponding amine alkene ester 6a. Thus hydrogenation of the triple bond to the double bond in the presence of a suitable catalyst, preferably Lindlar's catalyst, is carried out in an organic solvent such as dimethylformamide, and in the presence of ethylenediamine. The reaction is complete within 6 hours. The amino alkene ester is treated with HCl to provide the HCl salt.

In the last step, the amino alkene ester 6a is coupled with the benzothiophenecarboxylic acid 7 using conventional amide formation reaction. The acylation may be accomplished using the acid or an acylating equivalent thereof, such as the acid chloride or the acid anhydride. Preferably, the acid is used in conjunction with one or more coupling agent such as dicyclohexylcarbodiimide, 1-(3-dimethylaminopropyl)-3-ethylcarbodiimide (EDC), and hydroxybenzotriazole. The coupling reaction is carried out in the presence of a base such as diisopropylethylamine (DIPEA or Hunig's base) and in an organic solvent such as tetrahydrofuran. The ester is then converted to the acid by base-catalyzed hydrolysis, which is carried out at elevated temperature, e.g. about 40° C.

REFERENCE EXAMPLE 1

Preparation of 5-hydroxy-3-benzo[b]thiophenecarboxylic acid

Step 1. Preparation of 4-methoxy-1-propargylthiobenzene

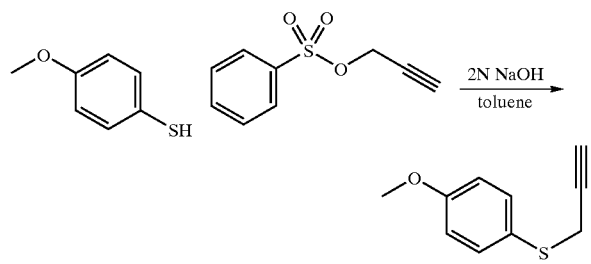

4-Methoxybenzenethiol (4.4 Kg) was added to a 100-L cylindrical flask equipped with an overhead stirrer, nitrogen inlet, and temperature probe. Toluene (44 L) was added, and the mixture was purged with nitrogen (sub-surface) for approximately 10 minutes at room temperature. Sodium hydroxide (2N, 20.4 L) was then added drop-wise to the thiol/toluene solution over 15–20 minutes at room temperature, with stirring, under a nitrogen atmosphere. The reaction mixture was heated to 40° C., and aged for 15 minutes. After the age period, propargyl benzenesulfonate (6.28 Kg) was added slowly, while maintaining the reaction temperature at 40° C. The reaction mixture was aged under nitrogen with stirring at 40° C., until completion. (approximately 2–3 hrs), then cooled to 40° C. and the layers cut after a 30 min settle time. The organic layer was washed with water (8.8 L×3) until the pH of the final aqueous wash was 7–8 The washed solution was used 'as is' in the next step.

Step 2. Preparation of 4-methoxy-1-propargylthiobenzene sulfoxide

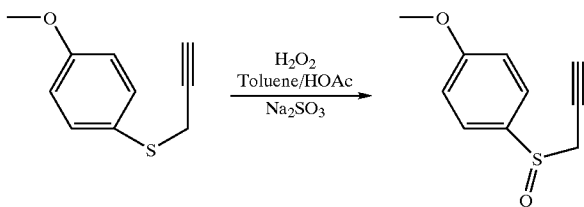

To the propargyl sulfide in toluene from Step 1 (50 L) was added 25 L acetic acid and then the solution was warmed to 40° C. Hydrogen peroxide (30%; 3.5 Kg) was then added over 1–2 h and the reaction mixture aged until the reaction was complete. The solution was cooled to 20° C. and sodium sulfite (10%; 7.05 Kg) was added to quench the excess peroxide. A solution of 25% brine (45 L) was then added. The layers were separated and the aqueous layer extracted once with toluene (2×25 L). The combined organic layers were then dried azeotropically under vacuum (t<30 C.) until the Kf was less than 60 ug/ml by Karl Fisher titration. The solution was assayed for yield. (98%).

Step 3. Preparation of 5-methoxy-3-benzo[b]thiophenemethanol

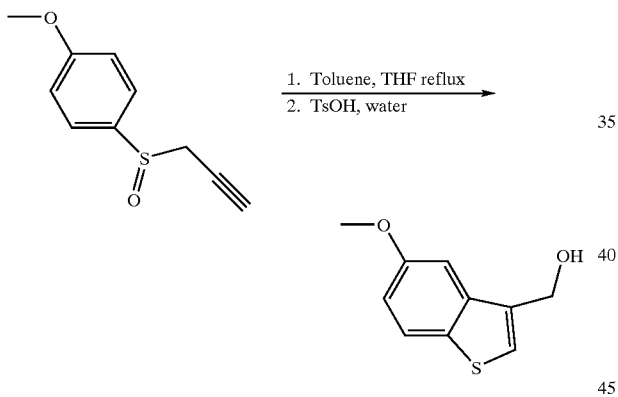

To the propargyl sulfoxide in toluene from Step 2 (25 L) was added tetrahydrofuran (25 L, Kf water content=180 ug/ml) and the mixture warmed to reflux (79° C.) for 5 hrs. The solution was then cooled to 20° C. and water (25 L) and p-toluenesulfonic acid (50 gm) were added. The mixture was aged at reflux (70° C.) for 4–5 hours until the thioacetal was converted to the allyl alcohol. The solution was neutralized with 2.5N NaOH (2 L) and 2.5 Kg sodium chloride was added. The organic layer was cut from the aqueous, drummed and assayed for yield.

Step 4. Preparation of 5-methoxy-3-benzo[b]thiophenecarboxaldehyde

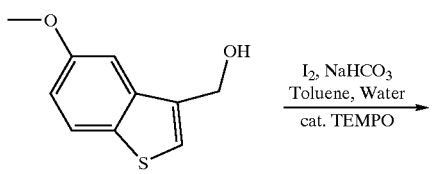

-continued

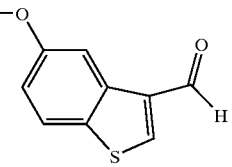

To the benzo[b]thiophene alcohol in toluene/THF from Step 3 was added NaHCO$_3$ (3.0 kg) and water (30 L) and aged until the bicarbonate was dissolved. Iodine (6 kg) was added and aged 1 hr at room temperature. TEMPO (2,2,6,6-tetramethyl-1-piperidinyloxy, free radical, 140 g) was then added. The mixture was aged at 23° C. for about 2–6 hours until the starting material was consumed.

The reaction mixture was cooled to ambient temperature and then 10% aq. Na$_2$SO$_3$ (15 L) was added to quench the excess iodine. The layers were cut and the organic layer washed with water (15 L). The organic layer was washed once with 2.2 kg 10% aq carbonate and then 2 kg water.

Step 5. Preparation of 5-methoxy-3-benzo[b]thiophenecarboxylic acid

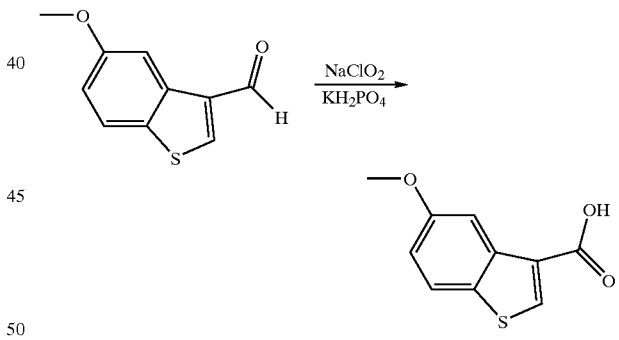

To the benzo[b]thiophene aldehyde from Step 4 in isopropyl acetate (30 L) at 20° C. was added KH$_2$PO$_4$ (2.1 kg) in water (10.5 L) and then 0.5 kg of 30% hydrogen peroxide. Sodium chlorite (1.95 kg), as a solution in water (20 wt %), was then added over several hours along with concurrent addition of more hydrogen peroxide (1.27 kg). After complete addition, the mixture was aged at 20° C. for approximately 6 h. The reaction mixture was maintained at 20–25° C. while 10% aq. Na$_2$SO$_3$ (15 kg) was added to quench the excess peroxide. 10% Na$_2$CO$_3$ (17 kg) was then added and the layers were cut. The organic layer was washed with 10% Na$_2$CO$_3$ (5 kg) to further extract the product into the aqueous layer. The aqueous layers were combined and washed once with isopropyl acetate (5 kg). The aqueous layer was then acidified to pH=5–6 with conc.HCl to crystallize the acid. The slurry was then filtered and the cake washed with water and partially dried on the filter pot. The resultant wet solid (appox. 10% water wet) was dissolved in THF (15 L).and then filtered into a batch concentrator through a 1 um in-line filter. The solution was solvent switched into toluene drying azeotropically (Kf=200 um) before cooling to 5° C., and filtering off the product.

Step 6. Preparation of 5-hydroxy-3-benzo[b]thiophenecarboxylic acid

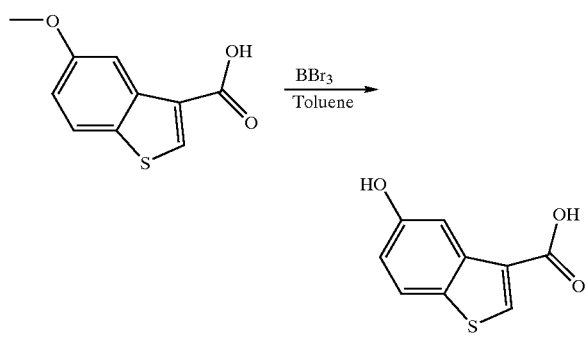

The methoxybenzo[b]thiophene carboxylic acid from Step 5 was slurried in toluene (35 L) and then warmed to 50° C. To an addition funnel containing toluene (9 L) was added boron tribromide (4.3 kg) and then the solution added over 1 hr to the slurry of 5-methoxy-3-benzo[b]thiophenecarboxylic acid. The mixture was aged for 8 hr. The reaction mixture was cooled to room temperature and 15%NaOH was slowly added (16 kg). To the three phase mixture was added 2 kg Solka Flok (filter aid) and then filtered to remove boric acid. The layers were then cut. To the aqueous layer was added 27 L THF and 4.5 kg NaCl, and then acidified to pH=1–3 with concentrated HCl (2.7 L). The layers were cut and the bottom layer extracted again with 15 L THF. The combined THF layers were then concentrated to a minimum stirred volume and solvent switched into toluene (kf<1000 ug/ml). The slurry was then cooled to 2–5° C., aged one hour and filtered, washing with cold toluene (10 L). The cake was dried on the filter pot with a nitrogen sweep under vacuum.

REFERENCE EXAMPLE 2

Preparation of ethyl 7-iodo-5-heptynoate

Step 1. Preparation of 6-chloro-1-(2-tetrahydropyranyl)oxy-2-hexyne

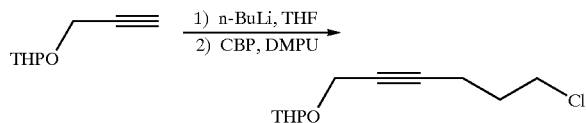

Tetrahydro-2-(2-propynyloxy)-2H-pyran (5.67 Kg, 40 moles) was dissolved in dry THL (28 L) and the mixture was cooled to approximately −30° C. n-Butyllithium (2.4 M in hexanes, 16.8 L, 40.0 moles) was added over 50 min while maintaining the temperature between −15 and −5° C. After completion of the addition, 1-bromo-3-chloropropane (CBP, 4.0 L, 40 mol) was added in one portion followed by the addition of 1,3-dimethyl-3,4,5,6-tetrahydro-2(1H)-pyrimidinone (DMPU 4.0 L, 33 moles) in one portion as well. The batch was allowed to warm to approximately 20° C. The reaction is exthothermic and the batch was cooled to keep the temprature between +40 and +45° C. and aged for 2 h, cooled to room temperature and pumped into a mixture of ethyl acetate (20 L) and 10% aqueous ammonium chloride (20 L). The layers were separated and the organic layer was washed with water (2×20 L). The organic layer was then concentrated (batch concentrator) to an orange oil that was used "as is" in the next step.

Step 2. Preparation of 6-cyano-1-(2-tetrahydropyranyl)oxy-2-hexyne

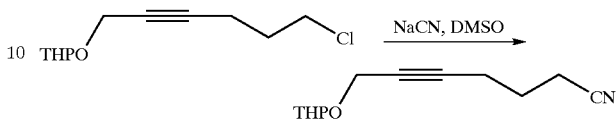

The crude product from Step 1 (6.57 Kg assay, 30.3 moles) containing excess bromochloropropane (approximately 6 moles) was dissolved in DMSO (28 L). Sodium cyanide (2.2 Kg, 45 moles) was added in one portion. The reaction was heated at +55° C. for approximately 10 hours, cooled to room temperature and diluted with toluene (28 L) and 1.5 wt % aqueous NaOH (28 L). The layers were separated, and the toluene layer was washed with 3% aqueous NaHCO₃ (2×22.5 L). The organic layer was then concentrated (batch concentrator) to yield a brown oil that was used "as is" for the next step.

Step 3. Preparation of 7-(2-tetrahydropyranyl)oxy-5-heptynoic acid

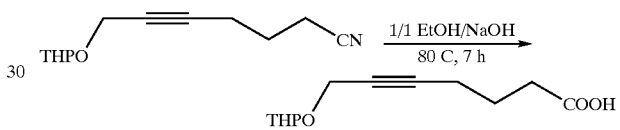

The crude THP-cyano compound from Step 2 (6.02 Kg assay, 29 moles) was dissolved in ethanol (18 L) and aqueous 5N sodium hydroxide (18 L, 90 moles). The reaction mixture was heated to reflux (approximately 80° C.) for 7 h, then cooled to room temperature, and diluted with methyl t-butyl ether (36 L) and water (15 L). The layers were separated and the organic layer was extracted with water (8.5 L). The combined aqueous layer (pH~13) was vigourously stirred with methyl t-butyl ether (36 L) at 5° C. 6N HCl (approximately 16 L) was added over 15 minutes maintaining the temperature below +25° C. until the pH became approximately 5.5. The layers were seaprated and the organic layer was washed with water (2×20 L). The aqueous cuts was back extracted with methyl t-butyl ether (18 L) for an extra 8% recovery of the acid. The organic layer was then concentrated (batch concentrator) to a brown oil that was used "as is" in the next step.

Step 4. Preparation of ethyl 7-hydroxy-5-heptynoate

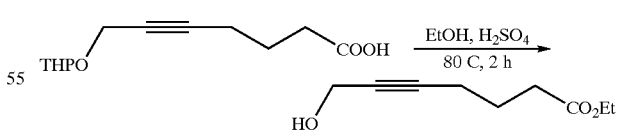

The crude THP-acid from Step 3 (6.19 Kg, 27.4 moles) was dissolved in absolute ethanol (38 L) and sulfuric acid (73 mL, 0.025 moles) was added. The reaction mixture was heated at reflux (approximately 80° C.) for 2 hours, cooled to approximately 40° C. and concentrated to less than a third of the original volume. The mixture was diluted with ethyl acetate (25 L) and water (25 L). The layers were separated and the organic layer was washed with 3% aqueous NaHCO₃ (2×18 L). The aqueous cuts were back extracted with ethyl acetate (12 L). The combined organic layers were then concentrated (batch concentrator) to a brown oil that was used "as is" for the next step.

Step 5. Preparation of ethyl 7-(methanesulfonyloxy)-5-heptynoate

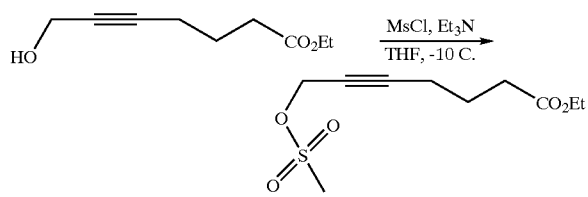

The crude hydroxy ester from Step 4 (3.99 Kg, 23.5 moles) was dissolved in dry THF (28 L) containing triethylamine (3.62 L, 25.8 moles) and the mixture was cooled to approximately −15° C. Methanesulfonyl chloride (2.0 L,25.8 moles) was added over 45 min while maintaining the temperature between −15° C. and −5° C. The reaction mixture was aged for one hour at 0° C. and then pumped into ethyl acetate (25 L) and 10% aqueous ammonium chloride (25 L). The layers were separated, and the organic layer as washed with water (2×20 L) and then concentrated (batch concentrator) down to an brown-orange oil that was used "as is" for the next step.

Step 6. Preparation of ethyl 7-iodo-5-heptynoate

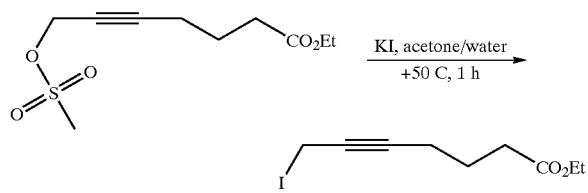

Crude mesylate ester from Step 5 (5.43 Kg, 21.9 moles) was dissolved in acetone (26.5 L) and water (4.7 L) and potassium iodide (4.17 Kg, 25.1 moles) was added in one portion. The reaction mixture was heated to +50° C. and aged for one hour, cooled to room temperature and diluted with toluene (28 L) and 5% aqueous NaHSO$_3$ (25 L). The layers were separated, and the organic layer was washed with water (2×20 L) then concentrated (batch concentrator) to a brown-orange oil that was used "as is" for the subsequent coupling with nopinone.

The following example illustrates the process of the present invention and is not to be construed as limiting the scope thereof in any manner.

EXAMPLE 1

Preparation of (5Z)-7-[(1R,2R,3S,5S)-2-(5-hydroxybenzo[b]thiophen-3-ylcarbonyl-amino)-6,6-dimethylbicyclo[3.1.1]hept-3-yl]hept-5-enoic acid Step 1. Coupling of (1R)-(+)-nopinone and ethyl 7-iodo-5-heptynoate

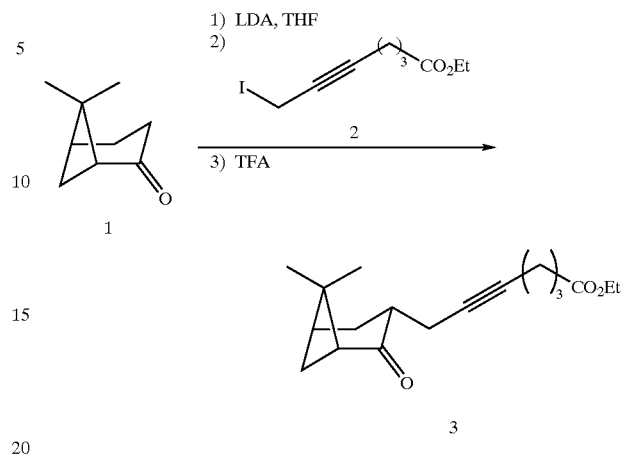

A 50 L round-bottomed flask was charged with dry THF (12 L) and diisopropylamine (2.23 L, 15.9 moles), and cooled to approximately −30° C. n-Butyllithium (2.4 M in hexanes, 6.34 L, 15.2 moles) was added over approximately 45 minutes maintaining the temperature between −15 and −10° C. After completion of the addition, the solution was aged for approximately 10 minutes and (1R)-(+)-nopinone (1, 2.0 Kg, 14.5 moles, neat) was added over approximately 45 minutes maintaining the temperature between −15 and −10° C. After completion of the addition, the solution was aged for approximately 15–30 minutes and cooled to −50° C. The iodo ester 2 (4.25 Kg assay, 15.2 moles) was added over approximately 1.5 hours maintaining the temperature between −48 and −45° C. After completion of the addition, the reaction mixture was aged for 1.5 hours between −48 and −45° C. Trifluoroacetic acid (TFA, 1.68 L, 21.7 moles) was then added over 1 hour maintaining the temperature below −45° C. The reaction mixture was allowed to warm to approximately −10° C. over 1 hour and pumped into ethyl acetate (20.0 L) and 3% aqueous L-tartaric acid (20.0 L). Layers were separated, and the organic layer was washed with water (2×20.0 L) then concentrated (batch concentrator) down to an orange oil that was used "as is" for the next step.

Step 2. Formation of the Oxime

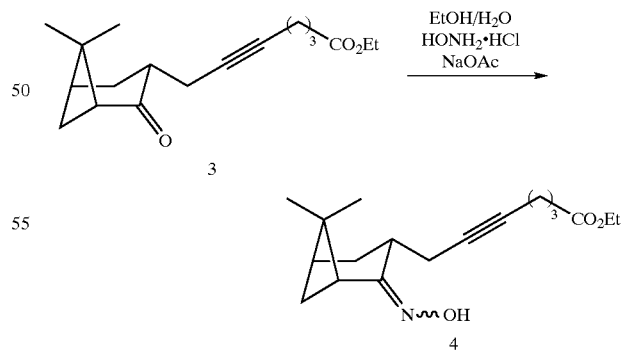

A 50 L round-bottomed flask was charged with the product of Step 1 (3, 3.874 Kg assay, 13.35 moles, d.e.= 98%), ethanol (13.0 L) and water (6.4 L). Sodium acetate trihydrate (3.631 Kg, 26.7 moles) was added followed by hydroxylamine hydrochloride (1.855 Kg, 26.7 moles). The reaction mixture was then heated to +50° C. (homogeneous)

for 5 hours, cooled to room temperature and pumped into toluene (20.0 L) and water (20.0 L). Layers were separated, and the organic layer was washed with water (2×20.0 L) then concentrated (batch concentrator) down to an orange oil that was used "as is" for the next step.

Step 3. Coversion of Oxime to Amine

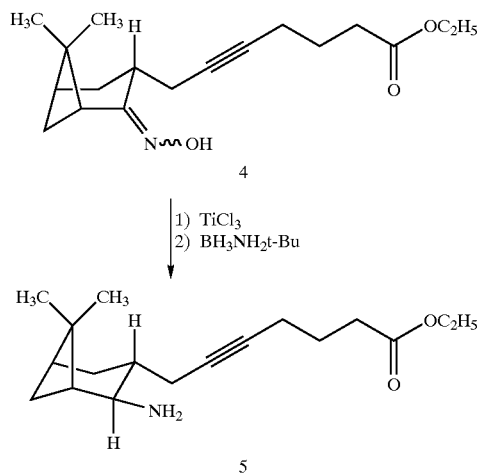

To a solution of aqueous TiCl₃ (20% in 3%HCl, ~1.4 M, 2.5 L, 3.5 mol) at 25° C. was charged 1.25 kg of sodium acetate trihydrate, and the mixture was stirred until all sodium acetate dissolves. Additional saturated sodium acetate was added to adjust pH to 1.0. The solution was cooled to 0° C. and the oxime of Step 2, (4, 305 g, 1 mol) in 2.5 L ethanol was added while maintaining the temperature at 0° C. The mixture was aged for 1 h, then solid borane t-butylamine complex (174 g, 2 mol) was charged over 10 min., maintaining the internal temperature<10° C. The resulting solution was aged for 30 to 60 minutes until no more imine intermediate remains. The reaction solution was extracted with ethyl acetate (5 L) and the phases were separated. The organic layer was washed with saturated ammonium chloride (2.5 L), neutralized with 1 M Na₂CO₃ until the aqueous pH was 8~8.5, and washed with water (2×2.5 L). The ethyl acetate solution was concentrated, solvent switched to isopropyl acetate (1 L) and azeotropically dried. HCl in ether (2.0 M, 0.6 L) was added and the mixture was concentrated to remove ether and any excess HCl. The volume was adjusted with isopropyl acetate to 1.5 L, the solution was seeded and n-heptane was added (1.5 L) over 1 h. The slurry was aged for 1 h and filtered. The cake was washed with a 1:1 mixture of isopropyl acetate/n-heptane (0.5 L) and dried to provide 5 as the HCl salt.

To an extractor containing isopropyl acetate (5 L) and 5 HCl (1 kg) was added Na₂CO₃ (1M, 3.5 L). The mixture was stirred for 1 h and the phases were separated. The organic layer was washed with NaHCO₃ (1M, 1.7 L), then with H₂O (3.5 L). The organic layer was concentrated to yield the crude 5 as an oil.

Step 4. Reductioin of Alkyne to Alkene

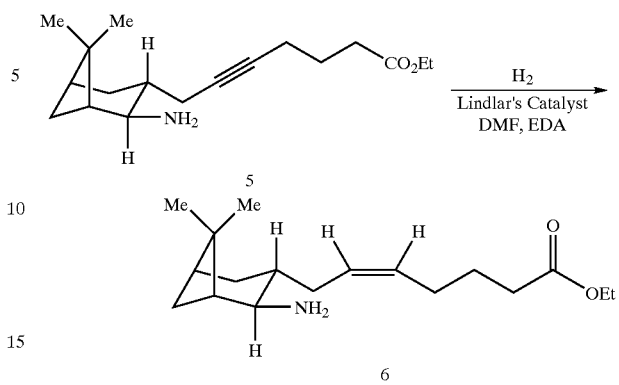

To a flask containing the aminoalkyne ester 5 (1 kg) was added, sequentially, dimethylformamide (DMF, 5.7 L), ethylene diamine (EDA, 0.914 L), and Lindlar's catalyst (40 g). The reaction was subjected to a hydrogen atmosphere (40 psi) for 6 h. The mixture was filtered to remove the catalyst, diluted with ethyl acetate (5.5 L) and washed with water (2×4.2 L). The organic layer was concentrated to yield an oil (1.0 kg).

To the flask containing the aminoalkene ester 6 (1 kg) in heptane (7.5 L) was added 1.83 M HCl in Et₂O (1.9 L) at 0° C. Upon complete addition the bath was removed and the mixture was allowed to warm to room temperature. The mixture was concentrated and then diluted with pure heptane (8 L). The mixture was heated to 60° C. or until complete dissolution of the solids. The mixture was allowed to cool and was stirred for 4 hours. The resulting slurry was filtered to yield the desired aminoalkene ester 6 as the HCl salt.

Step 5. Coupling with 5-hydroxy-3-benzo[b]thiophenecarboxylic acid

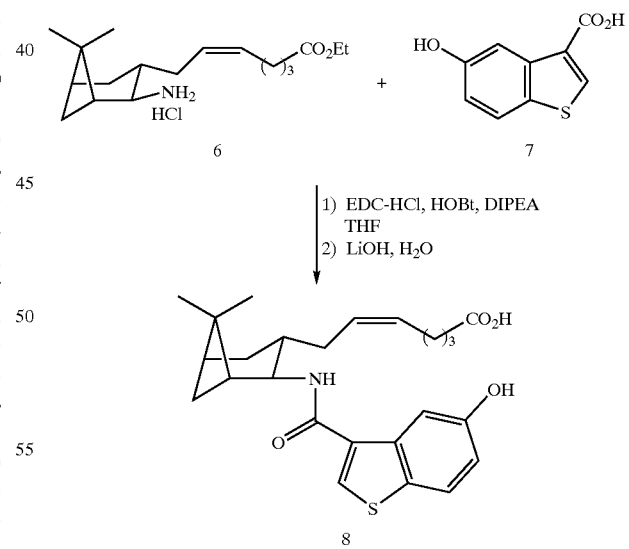

A 5 L round-bottomed flask was charged with the aminoalkene ester hydrochloride salt (6, 329.9 g, 1.0 mole), THF (2.86 L), 5-hydroxy-3-benzo[b]thiophenecarboxylic acid (7, 213.5 g, 1.1 moles), 1-(3-dimethylamino-propyl)-3-ethylcarbodiimide.HCl (250 g, 1.3 moles), 1-hydroxy benzotriazole hydrate (HOBT, 13.5 g, 0.1 mole), and Hunig's base (366 mL, 2.1 moles). The reaction mixture was aged at room temperature for approximately 10 hours, then diluted with water (715 mL). Lithium hydroxide monohydrate (210 g, 5.0 moles) was added in one portion and the reaction mixture was then heated to +40° C. for 4 hours, cooled to room temperature and diluted with ethyl acetate (2.0 L). The biphasic system (pH~12) was vigourously stirred and neutralized to pH~2.0 by the dropwise addition of 6N aqueous HCl (approximately 0.9 L) while maintaining the temperature below +25° C. The layers were separated, and the organic layer was washed with water (2×1.5 L) then concentrated (batch concentrator) to approximately 5 L per Kg assay (2.2 L ethyl acetate). n-Heptane (1.0 L) was then added, the mixture was seeded with 8 (4.4 g, 1%) and aged for 30 min. More n-heptane (1.2 L) was added over 1 hour, and the slurry was aged for an additional hour and filtered. The cake was washed with 1:1 mixture of ethyl acetate:n-heptane (0.5 L) and dried to give crude title compound 8 as an off white solid (397 g, 90%)

The crude product (442 g, 1 mol) was dissolved in methanol (2.2 L) and the solution was filtered through 1 micron filter to remove any solid. Water (0.44 L) and seed (22 g, 5%) were added and the mixture was aged for 30 min. More water (1.76 L) was then added over 1 hour. The slurry was aged for another hour and filtered. The resulting cake was washed with a 1:1 mixture of methanol/water (0.5 L) and dried under vacuum to give the pure title product 8 (420 g).

What is claimed is:

1. A process for the preparation of a compound of formula 8 or a salt thereof,

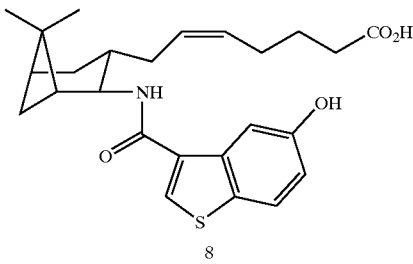

8 which comprises the steps of:

(1) treating the compound (1R)-(+)-nopinone with a strong base to generate the corresponding enolate;

(2) reacting the enolate with X—$CH_2$—C≡C—($CH_2$)$_3CO_2R$ where X is a leaving group and R is $C_{1-5}$alkyl to provide the compound 3a

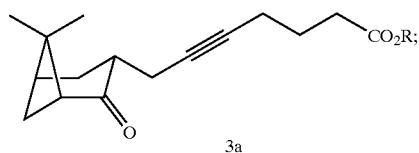

3a (3) reacting compound 3a with hydroxylamine to provide compound 4a

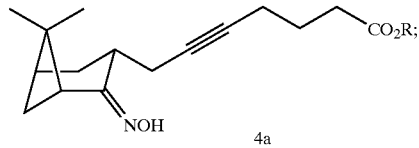

4a (4) treating compound 4a with titanium (III) chloride and a borane reagent to provide compound 5a

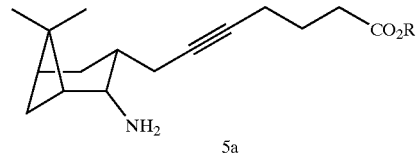

5a (5) treating compound 5a with hydrogen in the presence of a hydrogenation catalyst to provide compound 6a

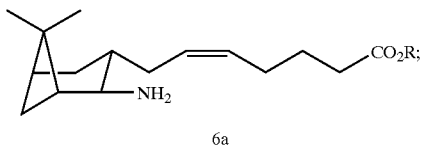

6a (6) reacting the compound 6a with 5-hydroxy-4-benzo[b]thiophenecarboxylic acid in the presence of coupling agent, or an acylating equivalent thereof, followed by base-catalyzed hydrolysis to provide compound 8.

2. A process of claim 1 wherein X—$CH_2$—C≡C—($CH_2$)$_3CO_2R$ is ethyl 7-iodo-5-heptynoate.

3. A process of claim 1 wherein in step (5) said hydrogenation catalyst is Lindlar's catalyst.

4. A process of claim 1 wherein in step (6) compound 6a is reacted with 5-hydroxy-4-benzo[b]thiophenecarboxylic acid in the presence of 1-(3-dimethylaminopropyl)-3-ethylcarbodiimide and hydroxybenzotriazole.

* * * * *